US006280430B1

(12) United States Patent
Neftel et al.

(10) Patent No.: US 6,280,430 B1
(45) Date of Patent: Aug. 28, 2001

(54) SYRINGE DEVICE FIXABLE ON A FLASK

(75) Inventors: Frédéric Neftel, Lausanne (CH); Bernard Bouvier, Eragny (FR)

(73) Assignee: Debiotech S.A., Lausanne (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,735

(22) PCT Filed: Nov. 13, 1995

(86) PCT No.: PCT/FR95/01488

§ 371 Date: May 1, 1997

§ 102(e) Date: May 1, 1997

(87) PCT Pub. No.: WO96/14820

PCT Pub. Date: May 23, 1996

(30) Foreign Application Priority Data

Nov. 14, 1994 (FR) .................................................. 94 13605
Dec. 13, 1994 (FR) .................................................. 94 14973

(51) Int. Cl.[7] ..................................................... A61B 19/00

(52) U.S. Cl. ............................................. 604/411; 604/905

(58) Field of Search .................................... 604/411, 414, 604/198, 192, 201, 253, 190, 905, 183; 141/19, 383, 329, 330, 1, 2, 18; 206/365, 363

(56) References Cited

U.S. PATENT DOCUMENTS

| | | | | |
|---|---|---|---|---|
| 3,826,260 | | 7/1974 | Killinger . | |
| 3,826,620 | * | 7/1974 | Killinger . | |
| 3,977,555 | * | 8/1976 | Larson | 206/363 |
| 4,516,967 | | 5/1985 | Kopfer | 604/87 |
| 4,564,054 | * | 1/1986 | Gustavsson | 604/198 |
| 4,768,568 | * | 9/1988 | Fournier et al. | 604/415 |
| 4,976,701 | * | 12/1990 | Ejlersen et al. | 206/365 |
| 5,125,908 | | 6/1992 | Cohen | 604/196 |

* cited by examiner

*Primary Examiner*—Anhtuan T. Nguyen
(74) *Attorney, Agent, or Firm*—Wolf, Greenfield & Sacks, P.C.

(57) ABSTRACT

An assembly comprising a flanged flask and a syringe device fixable thereto is provided. The syringe device includes a guide member for cooperating with the body of the flask. The guide member includes a first end with an internal guide surface at its terminal portion and a fastening mechanism set back from the internal guide surface. The internal guide surface cooperates with the cylindrical body of the flask and the fastening mechanism attached to the flange of the flask. A second end of the guide member provides translational guidance to a syringe.

20 Claims, 6 Drawing Sheets

SYRINGE DEVICE FIXABLE ON A FLASK

BACKGROUND OF THE INVENTION

1. Field of the Invention

The present invention relates to a syringe device fixable on a flask, in particular a flask containing a liquid to be injected or a substance that has been lyophilized and that is to be mixed with a physiological liquid or with medication so that the mixture can be injected.

2. Description of Related Art

There exist known substances, particularly in the medical field, which need to be stored separately and which should be mixed only immediately prior to being injected into a patient, e.g. subcutaneously, intravenously, or into muscle. This applies in particular to medical substances which are prepared in lyophilized (freeze dried) form, or in powder form, and which need to be mixed with a solvent, e.g. physiological serum, for administration to a patient. In other cases, the two components that are mixed together may both be liquids, when the liquids cannot be stored for long periods of time when mixed together.

The most commonly used technique is to store the powder in a separate receptacle which is closed by a membrane or a leakproof plug that can be punctured by means of a needle. Then, using a syringe of standard type, a certain quantity of solvent is taken from a second receptacle and the appropriate quantity of solvent is injected into the first receptacle through the membrane. The content of the first receptacle is then mixed together and the same syringe is then used to suck up the mixture. The syringe is then ready for injecting the medication.

In other known techniques, the liquid, e.g. physiological serum, is already contained in the syringe. It then suffices to inject the liquid through the puncturable membrane into the receptacle containing the substance in powder form, to mix the substances together, and then suck the mixture back into the syringe.

However, that technique suffers from certain difficulties in use. In particular, when the flask containing the powder has a neck of small diameter, it is difficult to puncture the puncturable plug appropriately. An essential condition for extracting all of the liquid contained in the flask after the powder has been mixed with the solvent is for the puncturable plug to be punctured in its center and for the needle to be inserted as small a distance as possible into the flask. That also serves to avoid wetting the needle while mixing is being performed, thus leaving the needle in a condition suitable for being reused to inject the mixture into the patient. Unfortunately, as already mentioned, when the neck of the flask is of small diameter, this can be difficult to do. There also exists a non-negligible risk of the user, e.g. a nurse, pricking a finger while performing the above operation.

An object of the present invention is to provide a syringe device that is fixable on a flask and which ensures that the puncturable plug is punctured in its center and which also makes this operation very reliable and completely repeatable. Another object of the present invention is to provide such a device which can be fitted onto a flask commonly used for containing medicinal powders for mixing with a solvent, and in particular substances that have been lyophilized.

SUMMARY OF THE INVENTION

According to the invention, this object is achieved by a syringe device suitable for fixing on a flask that has a cylindrical body, an opening surrounded by a flange presenting a side face, and a puncturable plug closing said opening, the device being characterized in that it comprises a guide part suitable for co-operating with said flask, and a syringe provided with a needle and mounted to slide in said guide part, said guide part including an open first end having at its terminal portion a first internal guide surface suitable for co-operating with the cylindrical body of said flask, and fastening means for fastening said part to said flange, which means are set back relative to said first internal guide surface, said fastening means being activated while said device is being put into place on said flask, said guide part including a second end and a common portion suitable for receiving said syringe provided with means for providing guidance in translation to said syringe in said guide part in order to bring said syringe into an engaged position in which its needle punctures the puncturable membrane of the flask, said guide part also having a central orifice for allowing the end of said needle to pass through under the effect of said syringe moving in translation.

It will be understood that in this way, because of the presence of the guide surface at the end of the guide part co-operating with the cylindrical body of the flask over sufficient length, the guide part is accurately centered relative to the puncturable plug of the flask. Consequently, the end of the needle of the syringe is properly positioned facing the central portion of the puncturable plug of the flask, thereby enabling the plug to be punctured under optimum conditions when the syringe is pushed into the guide part. Also, since the syringe is guided in translation relative to the guide part, this ensures that the positioning of the needle relative to the plug is maintained while the syringe is moving. In addition, the presence of the fastening elements makes it possible to secure the guide part, and thus the syringe, to the flask, thus making it easier to maneuver the syringe relative to the flask. In particular, that makes it possible to monitor very accurately how far the syringe has been pushed into the guide part, and thus how far the tip of the needle has penetrated into the flask after the plug has been punctured, in order to ensure that such penetration is kept down to a minimum. Naturally, after the operation of mixing and then sucking the mixture back into the syringe, the syringe can be separated from the guide part.

Preferably, the first end of the guide part includes a second internal guide surface suitable for co-operating with the side wall of the flange of the flask, the fastening means being disposed between the first and second guide surfaces. The presence of these two guide surfaces makes it possible to reduce the length of the first guide surface while obtaining accurate centering of the guide part relative to the flask.

Also preferably, in a first embodiment, the means for guiding the syringe in translation in the guide part include sealing means for providing sealing between the inside face of the guide part and the body of said syringe.

In a second embodiment, the means for guiding the syringe in the guide part include at least one guide face formed in the inside face of the guide part and suitable for co-operating with a portion of the body of said syringe.

According to another characteristic of the invention, the guide part includes a plate element disposed substantially perpendicularly to the direction of displacement of the syringe and in which the central orifice is formed, the face of the plate directed towards the first end of the guide part being provided with a projecting annular rib surrounding the central orifice, whereby said rib is pressed against the plug of said flask while said fixing means co-operate with said flask.

Other characteristics and advantages of the present invention appear more clearly on reading the following description of various embodiments of the invention given as non-limiting examples.

BRIEF DESCRIPTION OF THE DRAWINGS

The description refers to the accompanying drawings, in which.

DETAILED DESCRIPTION OF THE INVENTION

Figure 1:
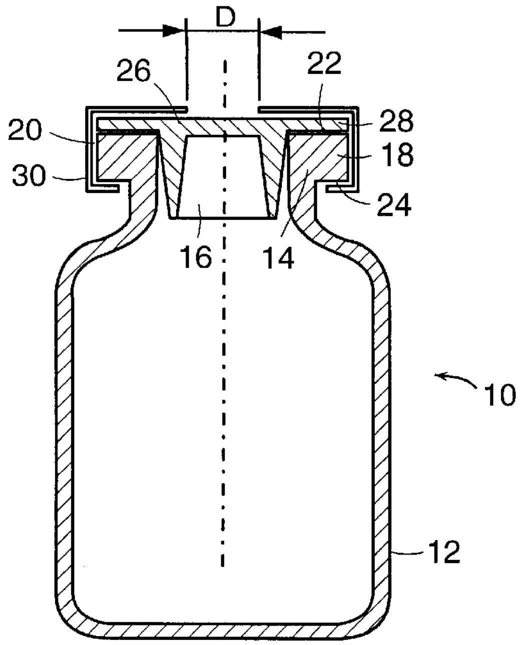
FIG. 1 is a vertical section through a flask usable with the syringe device of the invention.

With reference initially to FIG. 1, there is described a flask 10 of standard type e.g. containing medication in lyophilized form. The flask 10 comprises a cylindrical body 12 with a neck 14 defining an opening 16. The neck 14 is surrounded by a cylindrical flange 18 which has a side face 20, a top face 22, and an inside face 24. The flask is closed by a plug made of puncturable material 26 which is engaged in the opening 16 of the flask. The periphery 28 of the plug is pressed against the top face 22 of the flange, and a metal clamping capsule 30 fixes the plug in sealed manner onto the opening 16 of the flask 10.

It will be understood on looking at FIG. 1 that the diameter D of the puncturable central portion of the plug is relatively small, with its diameter lying in the range 5 mm to 2 mm, depending on the size of the flask.

Figure 2:
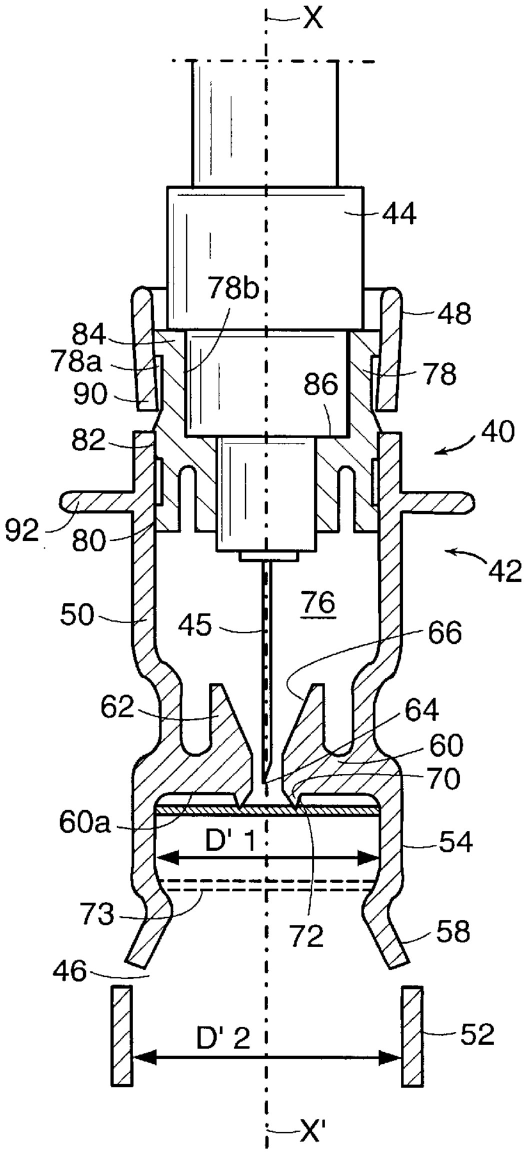
FIG. 2 is a section through a first embodiment of the syringe device.
Figure 2A:
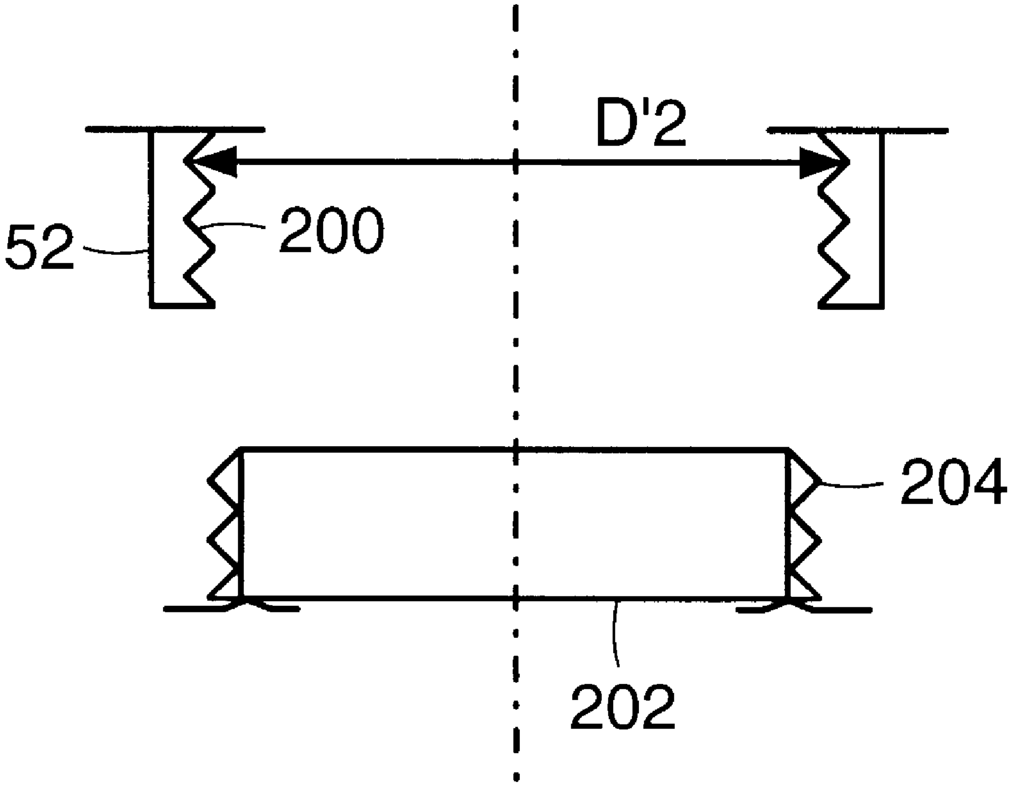
FIG. 2A illustrates a removable cap for use with a syringe device according to the invention
Figure 3:
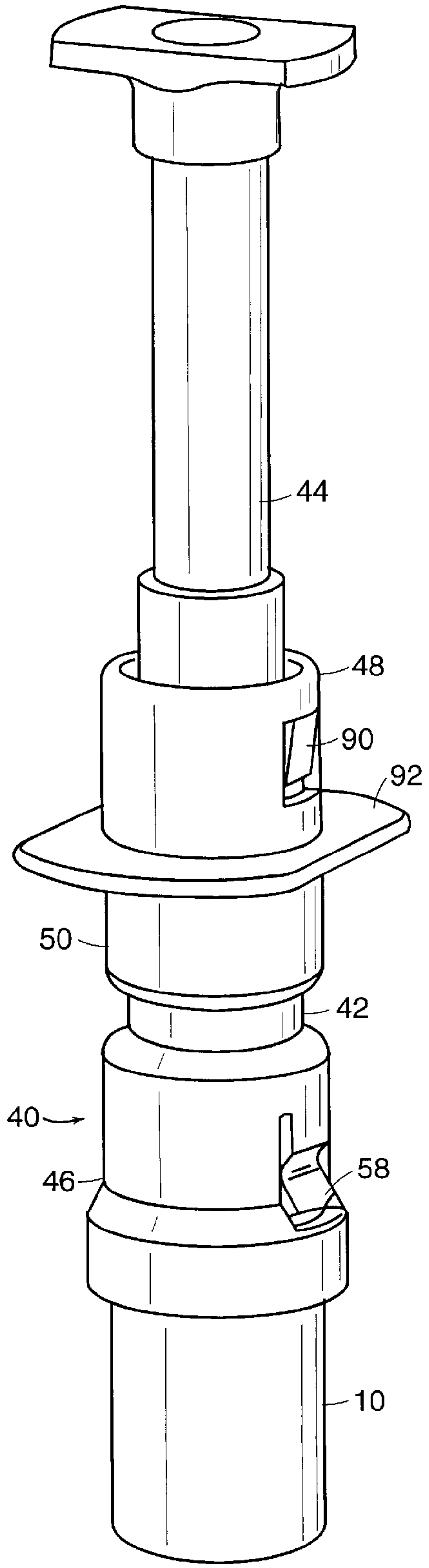
FIG. 3 is a perspective view of the syringe device fixed on a flask.
Figure 4A:
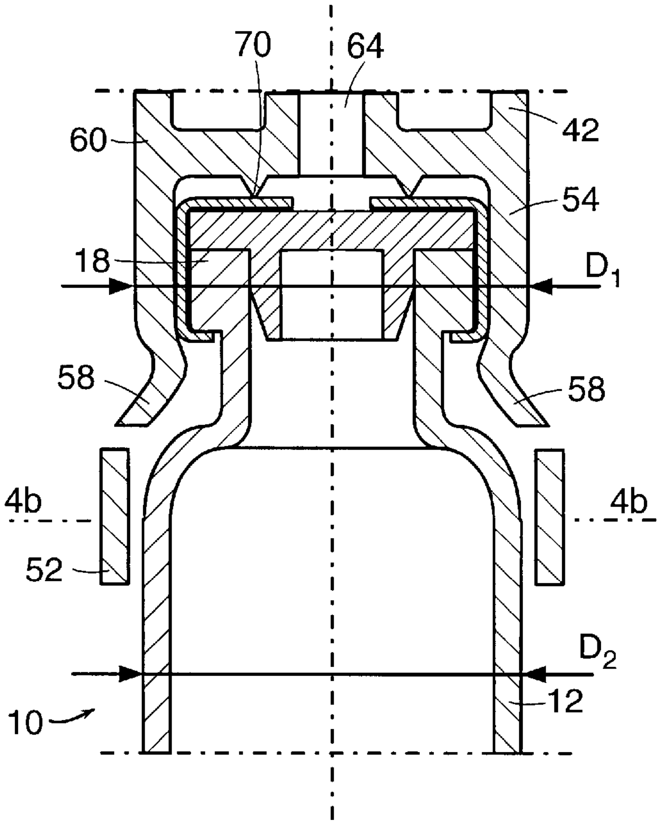
FIG. 4*a* is a detail view of FIG. 2 showing how the syringe device is fixed on a flask.

With reference now to FIGS. 2 to 4, there is described a first embodiment of a syringe device suitable for fixing on a flask of the kind shown in FIG. 1. The syringe device 40 is essentially constituted by a guide part 42 and a syringe 44 of conventional type fitted with a needle 45. The guide part 42 is preferably circularly symmetrical about the axis XX' and has a first end 46 for securing to the flask 10, a second end 48 for receiving and guiding in translation the syringe 44, and an intermediate common part 50. The first end 46 comprises a first guide surface 52 of inside diameter D'2 that is designed to co-operate with the cylindrical portion 12 of the flask, which has a diameter D2 that is slightly smaller than the diameter D'2. The end 46 includes a second circularly symmetrical guide surface 54 designed to co-operate with the side face 20 of the flange 18 of the flask, said guide surface having an inside diameter D'1 that is slightly greater than the diameter D1 of the flange 18. Between the guide surfaces 52 and 54, the end 46 of the guide part includes resilient snap-fastening elements 58 serving to secure the end 46 of the guide part 42 on the neck of the flask 10. As can be seen more clearly in FIGS. 2 and 4, the end 46 of the guide part is connected in its common portion by a portion 60 forming a plate that is substantially orthogonal to the axis XX' and that forms an integral portion of the guide part. This plate 60 is provided with an axial sleeve 62 which defines a central orifice 64 lying on the axis XX' of the guide part. The central orifice 64 is extended by a frustoconical portion 66 facing towards the second end of the guide part. When the syringe 44 is mounted on the guide part, the end of the needle 45 lies inside the central orifice 64. The bottom face 60*a* of the plate 60 is preferably provided with an annular rib 70 surrounding the orifice 64 and projecting from the face 60*a*. This ensures that the guide part 42 is secured to the flask, with the resilient tongues 58 co-operating with the bottom face 24 of the flange when the rib 70 is pressed against the plug. Accurate fixing and good sealing is thus obtained between the plug and the guide part by the action of the rib on the resilient material forming the plug of the flask. Also preferably, although not essentially, a puncturable membrane 72 can be fixed to the face 60*a* of the plate 60, thereby sealing the zone 76 inside the guide part, and thus ensuring that the space 76 containing the needle is kept sterile.

It will be understood that because of the presence of the resilient tongues 58, the guide part is automatically secured to the neck of the flask merely by pushing the neck of the flask into the end of the guide part, without there being any need for some other action being performed. The resilience of the tongues 58 ensures that they operate automatically.

It would not go beyond the invention if the guide surface 54 were to be omitted. Under such circumstances, the surface 52 would need to be of adequate length in the direction of the axis XX', e.g. 5 mm, so that it is capable, on its own, of positioning the guide part on the flask.

Figure 4B:
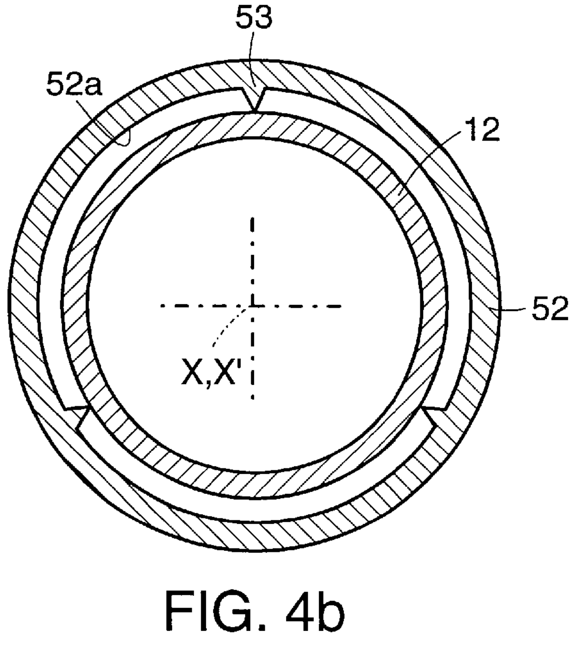
FIG. 4*b* is a horizontal section view on line B—B of FIG. 4*a;*

FIG. 4*b* shows a variant embodiment of the guide surface 52 and optionally of the guide surface 54. It makes it possible to achieve very good centering of the guide part 42 on the flask in spite of dimensional tolerances applicable to the flask. The inside face 52*a* of the guide surface is provided with at least one longitudinal rib 53, and preferably with three such ribs disposed at 120° intervals, and of a section that is triangular or similar. The edges of said ribs can be crushed to some extent along a diameter of the particular cylindrical body concerned, or of the flange, while still maintaining centering.

In dashed lines, FIG. 2 shows another variant embodiment of the guide part. In this variant, the puncturable membrane 72 is replaced by a film 73 (shown in dashed lines in the figure) whose periphery is fixed in sealed manner to the guide part 54. This very thin sealed film has tear starters in its center. When the guide part is put into place on the flask, the plug of the flask applies pressure to the film 73, thereby causing it to tear in its center. This ensures that the needle can pass through it freely.

To maintain sterile conditions in the inside zone 76 of the guide part, it is also possible to provide the inside face of the guide zone 52 with tapping 200. A removable cap 202 having an outside thread 204 can then be screwed to the end of the guide part.

The syringe 44 is guided in translation inside the common portion of the guide part by means of an annular sealing ring 78 whose outside face 78*a* preferably has three sealing ribs 80, 82, and 84 that co-operate with the guide part. The inside face 78*b* of the sealing ring 78 has a shoulder 86 co-operating with the syringe body 44. Consequently, the sealing ring is entrained by the syringe when the syringe is pushed into the guide part. In contrast, the sealing ring is free relative to the syringe when the syringe is moved to be extracted from the guide part. The end 48 of the guide part preferably includes resilient blades 90 projecting into the inside of the guide part. In the storage position, as shown in FIG. 2, the ends of the resilient blades 90 are interposed between the ribs 82 and 84 that serve to hold the sealing ring 78 to some extent relative to the guide part. In this way, the syringe and the guide part are indeed secured mechanically to each other by means of the sealing ring 78 which also serves to provide dynamic sealing between the guide part and the syringe body. As also shown in FIG. 2, the guide part 42 preferably has a flange 92 on its outside face serving to protect the fingers of people handling the equipment while the syringe is being put back into its initial place inside the guide part after it has been used.

Figure 5:
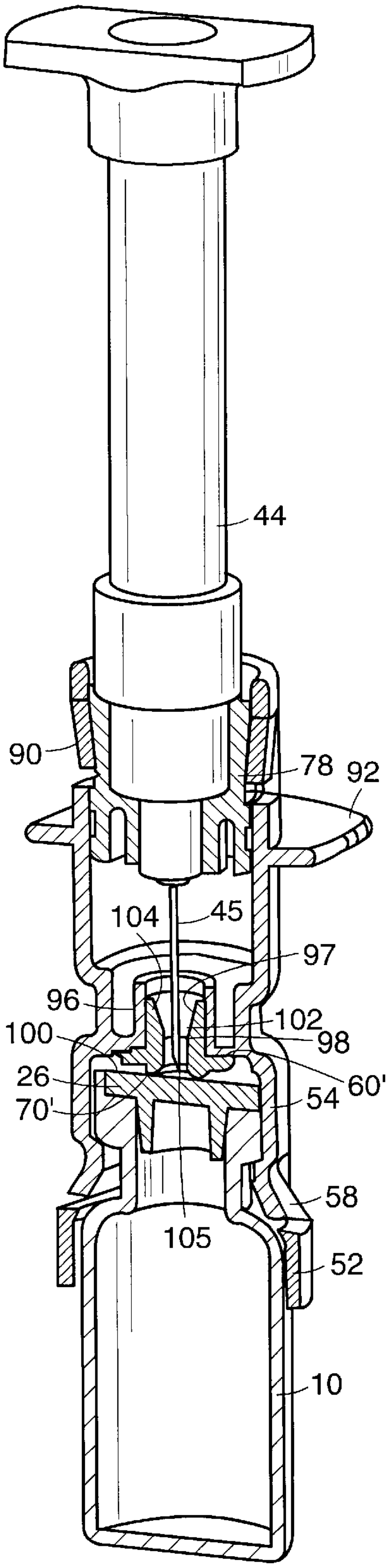
FIG. 5 is a view partially in perspective and partially in vertical section, showing a second embodiment of the syringe device fixed on a flask.

FIG. 5 shows a variant embodiment of the guide device. This variant consists solely in another embodiment of the plate 60 and of the sleeve 62. In this embodiment, the plate element which is now referenced 60' has a cylindrical sleeve 96 defining an axial bore 97 of large dimensions. In this axial bore, there is engaged an additional part 98. This part 98 includes a plate-forming portion 100 provided with the rib 70'. The additional part 98 also includes a sleeve-forming portion 102 which is engaged in the cylindrical sleeve 96. The sleeve 102 has a frustoconical end 104 and the central orifice 105, in similar manner to the sleeve 62 including a frustoconical end 66. It will be understood that when the extra part 98 is put into place in the sleeve 96, a structure is reconstituted which is identical to that shown in FIG. 2. The advantage of this technique lies in the fact that during the preliminary operations of preparing the syringe device, the syringe 44 is placed initially in the guide part 42 while the guide part is not yet provided with the part 98, after which the part 98 is installed via the first end of the guide part.

Figure 6A:
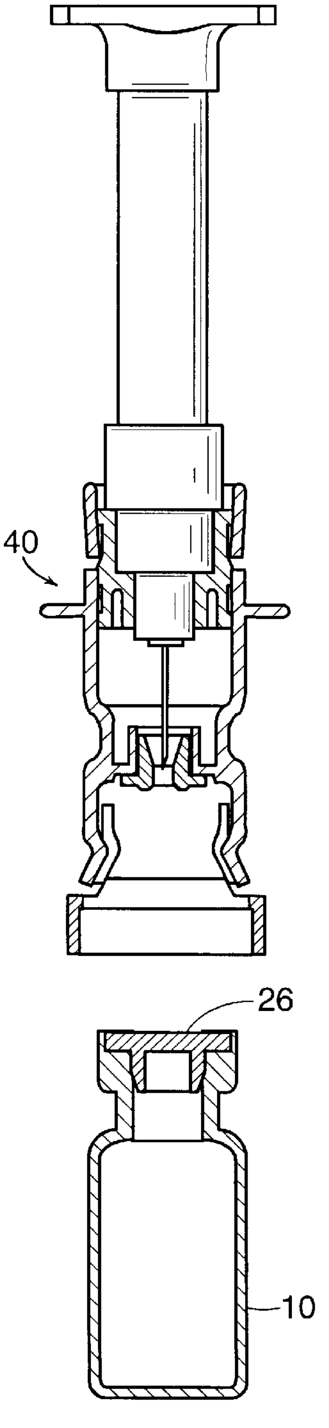
FIGS. 6*a* to 6*c* show how the syringe device is used.
Figure 6B:
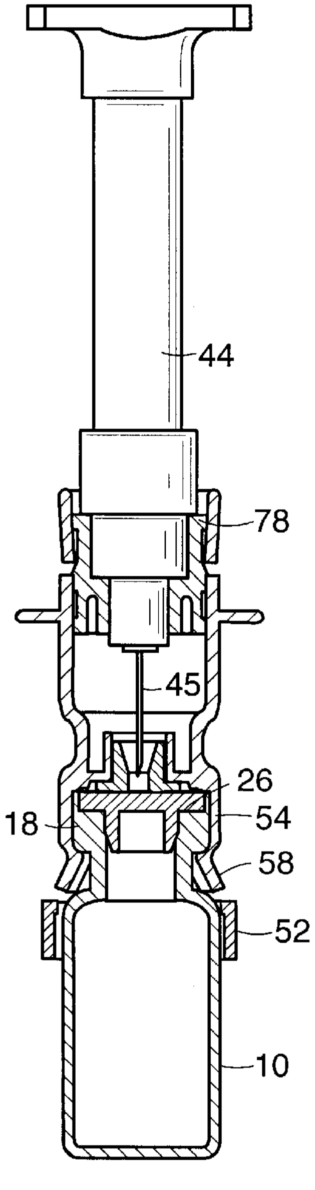

FIGS. 6*a* to 6*b* show the syringe device in use. FIG. 6*a* shows both the syringe device 40 and the flask 10 together with its puncturable plug 26.

FIG. 6*b* shows the syringe device 40 being put into place on the flask 10. The guide part 42 is accurately positioned relative to the flask and thus relative to the plug by means of the guide surfaces 52 and 54. In addition, the snap-fastening tongues 58 co-operate with the flange 18 of the flask, thereby holding the two parts together.

Figure 6C:
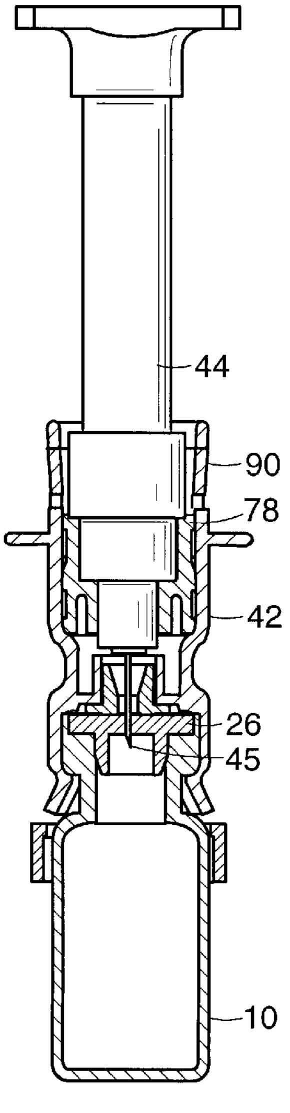

FIG. 6*c* shows the syringe being pushed into the guide part 42. This is controlled by the presence of the sealing ring 78. The needle 45 punctures the center of the plug 26. It is then possible, by actuating the piston of the syringe, to cause the liquid contained in the syringe to penetrate into the flask 10. After the two substances have been mixed together, the mixture prepared in this way is sucked back into the syringe. Thereafter it suffices to extract the syringe 44 from the guide part 42, with the sealing ring 78 remaining captive in the guide part because of the presence of the resilient tongues 90.

In addition, in both of these first two embodiments, the syringe is guided in translation in the guide part by means of the sealing ring 78 which also serves to provide sealing, and thus to ensure that the volume 76 containing the needle is kept sterile. These two functions could be obtained by providing for the syringe body 44 itself to have several, e.g. three, annular ribs that are spaced apart axially and that co-operate with the inside face of the common portion of the guide part.

Figure 7:
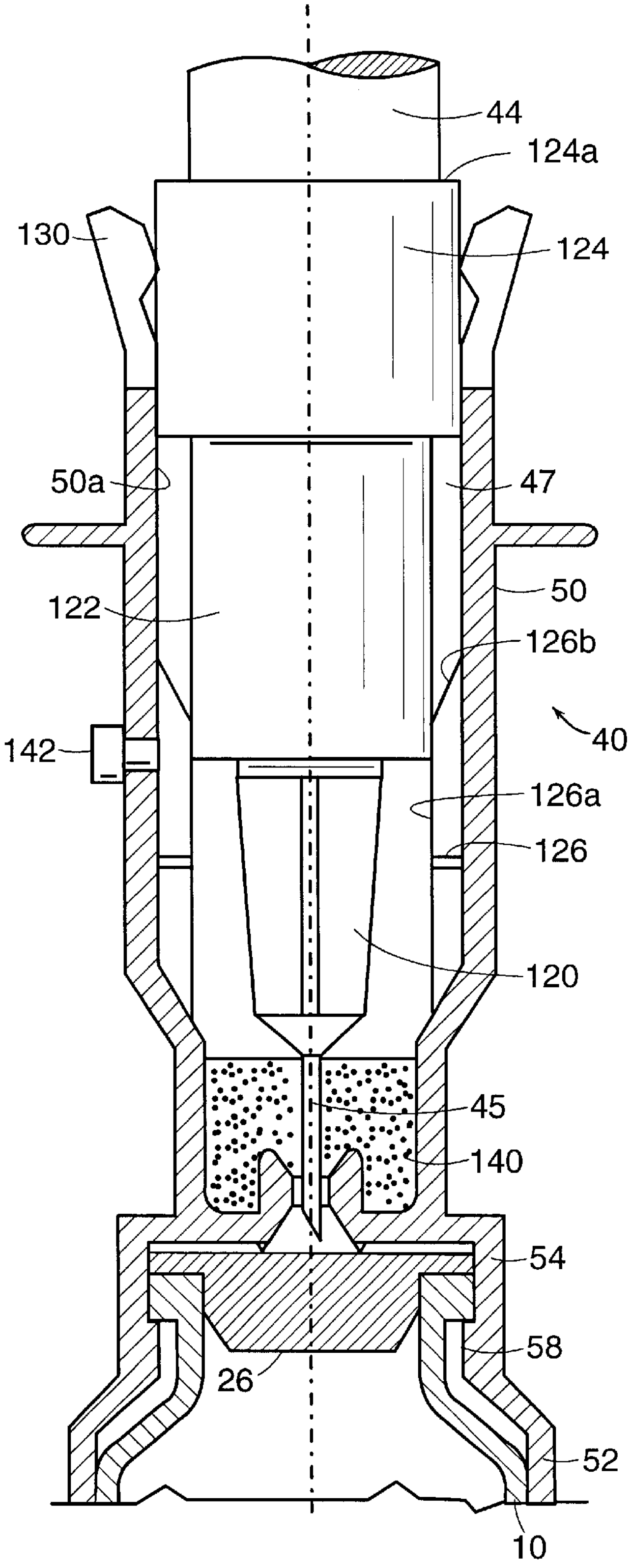
FIG. 7 is a fragmentary vertical section through a third embodiment of the syringe device.

With reference now to FIG. 7, there follows a description of a third embodiment of the syringe device. It differs from the first embodiment essentially by the fact that the sealing ring 78 is omitted and by the fact that the syringe 44 is guided in translation in the guide part 42 by means specifically provided for that purpose. The remainder of the device is identical in both cases and is therefore not described again.

Guidance in translation is provided by co-operation between internal guide surfaces of the guide part and certain portions of the body 47 of the syringe. In the example shown in FIG. 7, the end of the body 47 on which the needle 45 is mounted presents an endpiece 120, a small diameter cylindrical portion 122, and a cylindrical portion 124 of diameter larger than that of the common portion of the syringe body.

The inside face 50*a* of the common part 50 of the guide part has a diameter that is slightly greater than the outside diameter of the portion 124 of the syringe body, thereby forming a first guide surface. Inside the guide part there are provided four radially-extending guide fins 126 whose edges 126*a* are disposed on a circularly cylindrical surface whose diameter is slightly greater than that of the portion 122 of the syringe body. This defines a second guide surface. The distance between these two guide surfaces is large enough to provide very good guidance in translation of the syringe within the guide part, and thus accurate centering of the needle 45 relative to the plug 26.

Naturally, only one surface need be provided, on condition that it is of sufficient length.

It can also be seen that the top ends 126*b* of the fins 126 constitute an abutment against further pushing in of the syringe by co-operating with the large-diameter portion 124 of the syringe body. This abutment ensures that after the syringe has been pushed into the guide part, the tip of the needle 45 has indeed passed through the plug 26 of the flask, but that it penetrates only very little into the flask. This figure also shows, at the top end of the guide part, reversible clip-forming tabs 130 suitable for co-operating with the shoulder 124*a* of the syringe body. The purpose of these tabs 130 is reliably to secure the syringe in translation with the guide part when the syringe is fully engaged in the guide part. This makes handling the rod for controlling the syringe piston more comfortable when injecting the liquid contained in the syringe and when sucking the mixture back out from the flask.

FIG. 7 shows another improvement which could be implemented equally well in both of the above embodiments. This improvement relates to recovering harmful gases that might possibly escape from the flask after the components have been mixed together. Because of the excess pressure that may result from making the mixture in the flask and from temporary and local deformation of the plug when the tip of the needle leaves the plug, harmful gases or a residual fraction of liquid can penetrate into the guide part and escape into the surrounding air.

To solve this problem, it is possible to place a part 140 of porous material such as a porous foam at the first end of the guide part. When the needle is being extracted from the flask, any gases escaping from the flask are absorbed, trapped, or blocked by the part 140. Naturally, the needle passes through the part 140.

For the same purpose, it is also possible to provide in the guide part 40 an orifice that is obstructed by a microporous filter 142 making it possible to compensate the excess pressure created by the escaping gases, by filtering said gases outside the guide part without their toxic components. This disposition is particularly advantageous if the quantity of gas created is large.

The filter also serves to compensate pressures inside and outside the guide part during movements of the syringe through the guide part.

It should be added that the syringe device of the invention serves not only to ensure that the needle of the syringe and the flask are accurately coaxial, but also to position the guide part accurately relative to the flask along the axis XX'. To monitor the extent to which the needle has penetrated into the flask, it therefore suffices to monitor the extent to which the syringe has penetrated into the guide part. This result can be obtained automatically by providing an abutment that limits the extent to which the syringe can be pushed into the guide part.

Although particular embodiments of the invention have been described in detail for purposes of illustration, various changes and modifications may be made without departing from the scope and spirit of the invention. Accordingly, the invention is not to be limited except as by the appended claims and equivalents thereof.

What is claimed is:

1. An assembly comprising:

a flask having a cylindrical body, the flask including an opening surrounded by a flange provided with a side face and a puncturable plug closing said opening;

a syringe device suitable for fixing on the flask, the syringe device including a guide part having a first open end provided with a terminal portion, a common portion and a second open end, the terminal portion being provided with a first cylindrical internal guide surface for cooperatively resting on the cylindrical flask body and with fastening means located between the first cylindrical internal guide surface and the common portion of the guide part, the fastening means being activatable to cooperate with a flange disposed on the flask when the guide part is connected to the flask to fasten the guide part to the flask; and a syringe having a body and a needle fixed to a first end of the syringe body, said needle being moveable together with the syringe body and being unconnected to said guide part to move independently of said guide part, the common portion of the guide part provided with internal guiding means for cooperatively guiding the body of the syringe when the syringe is moved from a first position where the needle is distant from the puncturable plug of the flask to a second position where the needle passes through the puncturable plug of the flask.

2. The assembly according to claim 1, wherein said first end of said guide part includes a second internal guide surface suitable for cooperating with the side face of the flange of the flask, said fastening means being disposed between said first guide surface and said internal guiding means.

3. The assembly according to claim 1, wherein said internal guiding means include sealing means for providing sealing between the inside face of said guide part and the body of said syringe.

4. The assembly according to claim 3, wherein said sealing means include a sealing ring whose outside face co-operates with said guide part and whose inside face co-operates with said syringe body.

5. The assembly according to claim 4, wherein said sealing ring is constrained to move in translation with said syringe while said syringe is being engaged into said guide part.

6. The assembly according to claim 1, wherein said syringe body includes annular ribs projecting from said syringe body for co-operating with the inside face of said guide part.

7. The assembly according to claim 1, wherein said guide part includes abutment forming means to limit the extent to which said syringe can be engaged in said guide part.

8. The assembly according to claim 13, wherein said guide part further includes, facing said orifice, a part made of porous material.

9. The assembly according to claim 1, wherein the needle is spaced from the puncturable plug on the flask when the syringe is in the first position and when the guide part is fastened to the flask by the fastening means.

10. A syringe device suitable for fixing on a flask having a cylindrical body, the flask including an opening surrounded by a flange provided with a side face and a puncturable plug closing said opening, the syringe device comprising:

a guide part having a first open end provided with a terminal portion, a common portion and a second open end, the terminal portion provided with a first cylindrical internal guide surface for cooperatively resting on the cylindrical flask body and with fastening means located between the first cylindrical internal guide surface and the common portion of the guide member, the fastening means being activatable to cooperate with a flange disposed on the flask when the guide part is connected to the flask to fasten the guide part to the flask; and a syringe having a body and a needle fixed at a first end of the syringe body, the common portion of the guide part provided with internal guiding means for co-operatively guiding the body of the syringe when the syringe is moved from a first position where the needle is distant from the puncturable plug of the flask to a second position where the needle passes through the puncturable plug of the flask, wherein said internal guiding means include sealing means for providing sealing between the inside face of said guide part and the body of said syringe, said sealing means including a sealing ring whose outside face cooperates with said guide part and whose inside face cooperates with said syringe body, and said guide part including single-direction locking means towards its second end and cooperating with said sealing ring to hold said sealing ring and said guide part together and to allow said sealing ring only to be engaged in said guide part.

11. A syringe device suitable for fixing on a flask having a cylindrical body, the flask including an opening surrounded by a flange provided with a side face and a puncturable plug closing said opening, the syringe device comprising:

a guide part having a first open end provided with a terminal portion, a common portion and a second open end, the terminal portion provided with a first cylindrical internal guide surface for cooperatively resting on the cylindrical flask body and with fastening means located between the first cylindrical internal guide surface and the common portion of the guide member, the fastening means being activatable to cooperate with a flange disposed on the flask when the guide part is connected to the flask to fasten the guide part to the flask; and a syringe having a body and a needle fixed at a first end of the syringe body, the common portion of the guide part provided with internal guiding means for cooperatively guiding the body of the syringe when the syringe is moved from a first position where the needle is distant from the puncturable plug of the flask to a second position where the needle passes through the puncturable plug of the flask, wherein said guide part includes at least a first guide face formed in the inside face of said guide part to cooperate with a portion of the body of the syringe, and reversible snap fastening means for temporarily securing said syringe to said guide part while said syringe is filly engaged in said guide part.

12. The assembly according to claim 11, wherein said internal guiding means include a second guide face formed in the inside face of the guide part for co-operating with another portion of the body of said syringe.

13. A syringe device suitable for fixing on a flask having a cylindrical body, the flask including an opening surrounded by a flange provided with a side face and a puncturable plug closing said opening, the syringe device comprising:

a guide part having a first open end provided with a terminal portion, a common portion and a second open end, the terminal portion provided with a first cylindrical internal guide surface for cooperatively resting on the cylindrical flask body and with fastening means located between the first cylindrical internal guide surface and the common portion of the guide member, the fastening means being activatable to cooperate with a flange disposed on the flask when the guide part is connected to the flask to fasten the guide part to the flask; and a syringe having a body and a needle fixed at a first end of the syringe body, the common portion of the guide part provided with internal guiding means for cooperatively guiding the body of the syringe when the syringe is moved from a first position where the needle is distant from the puncturable plug of the flask to a second position where the needle passes through the puncturable plug of the flask, wherein the first end of said guide part is provided with an annular rib surrounding a central orifice whereby said rib is pressed against the plug of said flask when the fastening means co-operate with said flask.

14. The assembly according to claim 13, wherein said guide part includes a plate element disposed substantially perpendicularly to the direction of displacement of the syringe and in which said central orifice is formed, the face of said plate directed towards the first end of said guide part being provided with said projecting annular rib surrounding said central orifice.

15. The assembly according to claim 13, wherein the fastening means include snap-fastening means suitable for co-operating with the face of the flange of the flask opposite from the face of the flange that receives said plug.

16. The assembly according to claim 13, wherein said central orifice is defined by a part that is added on and mounted in said first end of the guide part, said add-on part including a sleeve-shaped portion with one end that is flared, and a portion defining said annular rib surrounding said orifice.

17. The assembly according to claim 13, further including a puncturable membrane closing said central orifice.

18. The assembly according to claim 13, further including a thin film whose periphery is fixed in sealed manner to the inside wall of the first end of said guide part in its portion which extends between said fastening means and said central orifice, said film having tear starters, whereby said film is opened under the action of the plug of said flask when the syringe device is mounted on said flask.

19. A syringe device suitable for fixing on a flask having a cylindrical body, the flask including an opening surrounded by a flange provided with a side face and a puncturable plug closing said opening, the syringe device comprising:

a guide part having a first open end provided with a terminal portion, a common portion and a second open end, the terminal portion provided with a first cylindrical internal guide surface for cooperatively resting on the cylindrical flask body and with fastening means located between the first cylindrical internal guide surface and the common portion of the guide member, the fastening means being activatable to cooperate with a flange disposed on the flask when the guide part is connected to the flask to fasten the guide part to the flask; and a syringe having a body and a needle fixed at a first end of the syringe body, the common portion of the guide part provided with internal guiding means for cooperatively guiding the body of the syringe when the syringe is moved from a first position where the needle is distant from the puncturable plug of the flask to a second position where the needle passes through the puncturable plug of the flask, and further including a removable cap fixed in said first end of the guide part.

20. A syringe device suitable for fixing on a flask having a cylindrical body, the flask including an opening surrounded by a flange provided with a side face and a puncturable plug closing said opening, the syringe device comprising:

a guide part having a first open end provided with a terminal portion, a common portion and a second open end, the terminal portion provided with a first cylindrical internal guide surface for cooperatively resting on a cylindrical flask body and with fastening means located between the first cylindrical internal guide surface and the common portion of the guide member, the fastening means being activatable to cooperate with a flange disposed on the flask when the guide part is connected to the flask to fasten the guide part to the flask; and a syringe having a body and a needle fixed at a first end of the syringe body, the common portion of the guide part provided with internal guiding means for cooperatively guiding the body of the syringe when the syringe is moved from a first position where the needle is distant from the puncturable plug of the flask to a second position where the needle passes through the puncturable plug of the flask;

wherein the guide part includes in its side wall an opening that is closed by a microporous filter.

* * * * *